United States Patent
Furnish et al.

[19]

[11] Patent Number: 6,132,370

[45] Date of Patent: *Oct. 17, 2000

[54] RETRACTOR-MOUNTED CORONARY STABILIZER

[75] Inventors: Gregory R. Furnish, Lawrenceville; Christopher S. Looney, Roswell, both of Ga.

[73] Assignee: Genzyme Corporation, Cambridge, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/719,354

[22] Filed: Sep. 25, 1996

Related U.S. Application Data

[63] Continuation-in-part of application No. 08/639,214, Apr. 26, 1996.

[51] Int. Cl.[7] ........................................ A61B 17/00

[52] U.S. Cl. .......................... 600/235; 600/215

[58] Field of Search .................. 600/201, 210, 600/213, 214, 217, 226–228, 234, 235, 240

[56] References Cited

U.S. PATENT DOCUMENTS

| | | | |
|---|---|---|---|
| 810,675 | 1/1906 | Richter | 600/219 |
| 2,693,795 | 11/1954 | Grieshaber | 600/213 |
| 2,863,444 | 12/1958 | Winsten | 600/214 |
| 4,052,980 | 10/1977 | Grams et al. | 600/211 X |
| 4,461,284 | 7/1984 | Fackler | 128/20 |
| 4,754,746 | 7/1988 | Cox | 600/210 |
| 4,949,707 | 8/1990 | Le Vahn et al. | 600/228 X |
| 5,133,724 | 7/1992 | Wilson, Jr. et al. | 606/151 |
| 5,167,223 | 12/1992 | Koros et al. | 600/232 |
| 5,318,013 | 6/1994 | Wilk | 600/225 X |
| 5,498,256 | 3/1996 | Furnish | 606/1 |
| 5,529,571 | 6/1996 | Daniel | 600/213 X |
| 5,782,746 | 7/1998 | Wright | 600/37 |
| 5,795,291 | 8/1998 | Koros et al. | 600/232 |
| 5,846,187 | 12/1998 | Wells et al. | 600/201 |
| 5,846,193 | 12/1998 | Wright | 600/715 |
| 5,894,843 | 4/1999 | Benetti et al. | 128/898 |
| 5,984,865 | 11/1999 | Farley et al. | 600/213 |

FOREIGN PATENT DOCUMENTS 2233561  1/1991  United Kingdom ................... 600/234

OTHER PUBLICATIONS

Coronary Surgery Without Cardiopulmonary Bypass, British Heart Journal, 1995 pp. 203–205.

Triple Coronary Artery Revascularization on the Stabilized Beating Heart: Initial Experience, Montreal Heart Institute, 1997, pp. 283–288.

Snaring of the Target Vessel in Less Invasive Bypass Operations Does Not Cause Endothelial Dysfunction, The Society of Thoracic Surgeons, 1997, pp. 751–755.

Direct Myocardial Revascularization by Saphenous Vein Graft, The Society of Thoracic Surgeons, 1970, pp. 97–111.

"Cardiac Retractor for Coronary Bypass Operations," John A. Rousou, MD, et al., *The Annals of Thoracic Surgery*, 1991, 52: 877–78.

"A New Retractor to Aid in Coronary Artery Surgery," A.J. DelRossi, MD, G.M. Lemole, MD, *The Annals of Thoracic Surgery*, vol. 36, No. 1, 101–02, Jul. 1983.

(List continued on next page.)

*Primary Examiner*—Danton D. DeMille
*Assistant Examiner*—Denise Pothier
*Attorney, Agent, or Firm*—Richard D. Allison; Thomas J. DesRosier

[57] ABSTRACT

An apparatus for stabilizing a predetermined area on a heart or other organ of a patient to enable a surgical procedure, the apparatus comprising a bifurcated member having two elongated prongs and an elongated handle segment pivotally attached to the bifurcated member. The handle segment can be movably attached to a rib retractor or other surgical device so that a person is not required to hold the handle segment. The apparatus may further comprise an attachment or inlay to prevent lateral movement thereof when being used in the surgical procedure.

14 Claims, 5 Drawing Sheets

OTHER PUBLICATIONS

"New Helper Instrument in Cardiac Surgery," D. Roux, MD, et al., *The Annals of Thoracic Surgery*, 1989, 48: 595–6.

"Aortic Spoon–Jaw Clamp for Aorta–Saphenous Vein Anastomosis," Francis Robicsek, M.D., *Journal of Cardiac Surgery*, 1995; 10:583–585.

"Technique of Dissecting the Internal Mammary After Using the Moussalli Bar," R.I. Hasan, et al., *European Journal of Cardiothoracic Surgery*,4:571–572, 1990.

"Self–Retaining Epicardial Retractor for Aortocoronary Bypass Surgery," Victor Parsonnet, MD, et al., *The Journal of Thoracic and Cardiovascular Surgery*, 629–30, 1979.

"A New Internal Mammary Artery Retractor," M. Bugge, *Thoracic Cardiovascular Surgeon* 38, 316–17 (1990).

"A Simple, Inexpensive Method of Heart Retraction During Coronary Artery Bypass Surgery," G.D. Angelini, MD, M.Ch., F.R.C.S., *The Annals Thoracic Surgery* 46:246–47, Aug. 1988.

A New Device for Exposing the Circumflex Coronary Artery, Akio Matsuura, MD, et al., *The Annals of Thoracic Surgery* 1995; 59:1249–50.

"Correspondence and Brief Communications," *Archives of Surgery*, vol. 115, 1136–37, Sep. 1980.

"Internal Mammary Artery Dissection: A Three Dimensional Sternal Retractor," D. Roux, MD, et al., *Journal Cardiovasic Surgery*, 30, 996–97, 1989.

"Off–Bypass Coronary Bypass Grafting Via Mimithoracotomy Using Mechanical Epicardial Stabilization," Jochen Cremer, MD, et al., *The Annals of Thoracic Surgery* 1997; 63:S79–83.

"Single Coronary Artery Bypass Grafting—A Comparison Between Minimally Invasive 'Off Pump' Techniques and Conventional Procedures," Johannes Bonatti, et al., *European Journal of Cardio–Thoracic Surgery*, 14 (Suppl. I) (1998) S7–S12.

"Less Invasive Coronary Surgery: Consensus From the Oxford Meeting," Stephen Westaby, FRCS, and Federico J. Benetti, MD, *The Annals of Thoracic Surgery* 1996; 62:924–31.

"Mini–Sternotomy for Coronary Artery Bypass Grafting," Kit V. Arom, MD, PhD, et al., *The Annals of Thoracic Surgery* 1996; 61:1271–2.

"Limited Access Myocardial Revascularization," Denton A. Cooley, MD, Texas Heart Institute Journal, vol. 23, No. 2, 1996.

"Mini–Sternotomy for Coronary Artery Bypass Grafting," *The Annals of Thoracic Surgery*, 1996; 62:1884–85.

"The Cardiac Rag—Simple Exposure of the Heart," Michael M. Bedellino, MD, et al., *Texas Heart Institute Journal*, vol. 15, No. 2, 1988, 134–35.

"Fabric Heart Retractor for Coronary Artery Bypass Operations," Shigeru Kazama, MD,et al., *The Annals of Thoracic Surgery* 1993; 55:1582–3.

"Minimally Invasive Coronary Artery Bypass Grafting," Antonio M. Calafiore, MD, et al., *The Annals of Thoracic Surgery*, 1996; 62:1545–8.

"Improved Visualization of the Internal Mammary Artery with a New Retractor System," John Pittman, MD, et al., *The Annals of Thorac Surg*, 1989; 48:869–70.

"A Modified Sternal Retractor," Nelson Ancalmo, MD, and John L. Ochsner, MD, Aug. 8, 1975.

"A Versatile Retractor for Use in Harvesting the Internal Mammary Artery and Performing Standard Cardiac Operations," Steven J. Phillips, MD, and Marge Core, RN, *The Journal of Thoracic Surgery*, 1989; 97: 633–35.

"Surgical Management of Diseased Intracavitary Coronary Arteries," John L. Ochsner, MD and Noel L. Mills, MD, *The Annals of Thoracic Surgery*, vol. 38, No. 4, 356–62 (Oct. 1984).

"Technique of Internal Mammary—Coronary Artery Anastomosis," *The Journal of Cardiovascular Surgery*, 78: 455–79, 1979.

"Graduated Probes for Coronary Bypass Surgery," George E. Green, MD, *The Journal of Thoracic and Cardiovascular Surgery*, vol. 68, No. 3, 424–27 (Sep. 1974).

"A Modified Sternal Retractor for Exposure of the Internal Mammary Artery," Peter P. McKeown, MB,BS, et al. *The Society of Thoracic Surgeons*, 1980.

"A New Concept in Sternal Retraction: Applications for Internal Mammary Artery Dissection and Valve Replacement Surgery," Aurelio Chaux, MD, and Carlos Blanche, MD, *The Annals of Thoracic Surgery*, 473–74, Oct. 1986.

The Japanese Journal of Thoracic Surgery, 1987, vol. 40, No. 1, pp. 39–40 (translation of summary included).

"Heart Retractor," Japanese article (undated) (translation of summary included).

"Tecnica Operatoria," Minerva Cardioangiologica, vol. 23—N. 6–7 (1975) (translation of summary included).

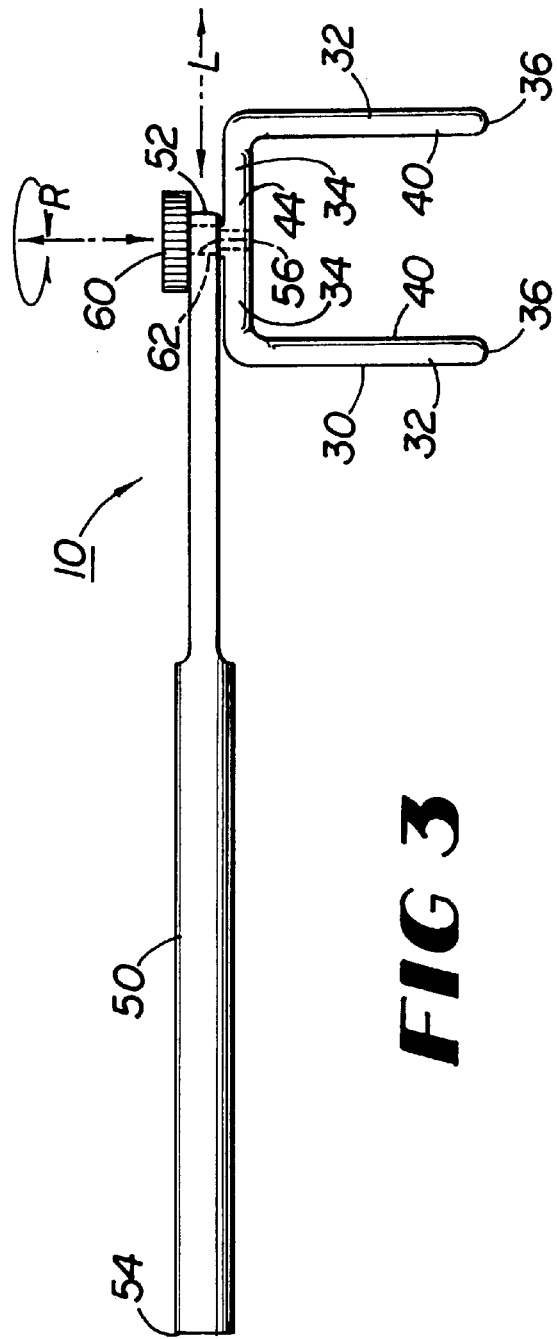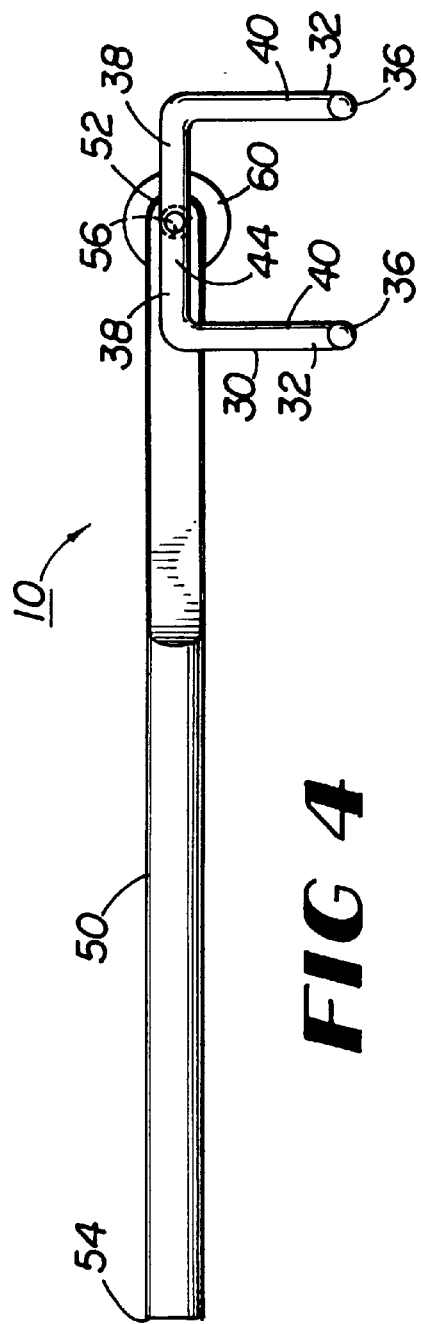

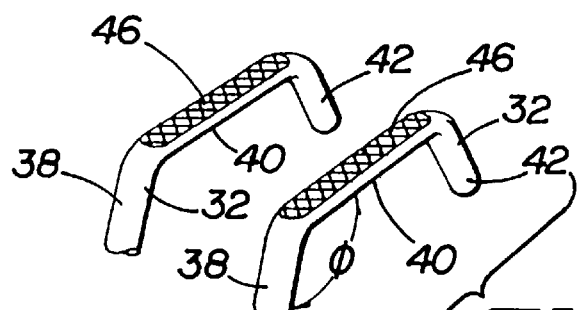
FIG 6
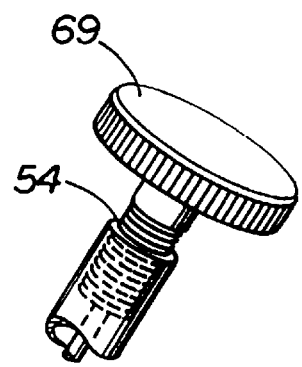
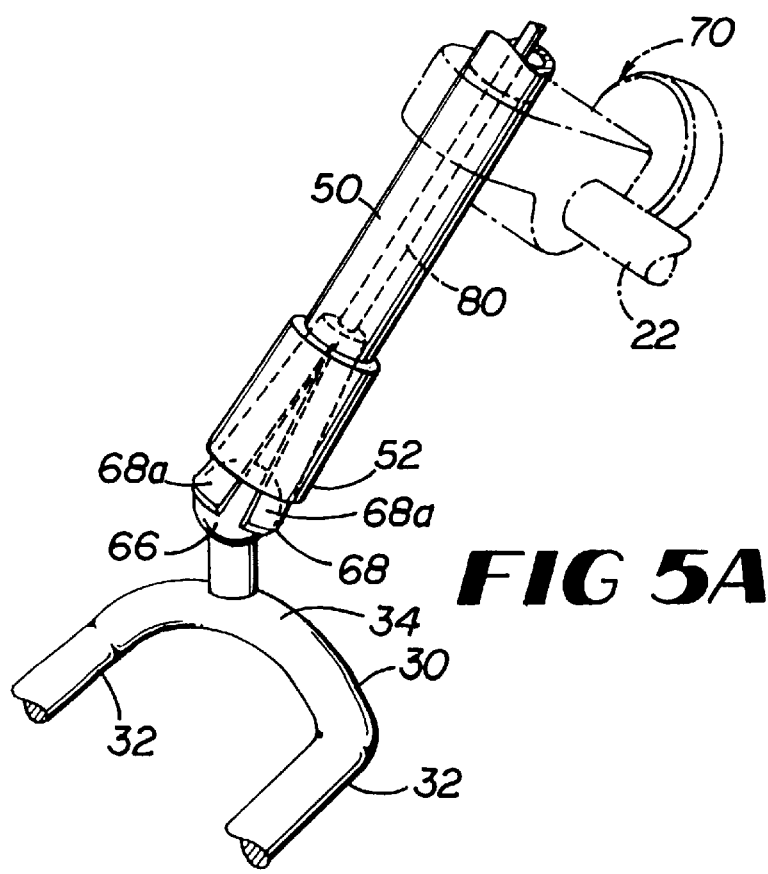
FIG 5A

RETRACTOR-MOUNTED CORONARY STABILIZER

This application is a continuation-in-part application of application Ser. No. 08/639,214, filed Apr. 26, 1996, which is pending.

BACKGROUND OF THE INVENTION

1. Field of the Invention

This invention relates to an apparatus for stabilizing a predetermined area of the body during surgical intervention, which better enables a surgeon to perform a surgical procedure at the surgical site. In particular, the invention relates to an apparatus for stabilizing a predetermined area of the heart for performing minimally invasive coronary artery bypass grafting at the surgical site, in which the apparatus is adapted to be connected to a rib retractor and has a pivotal joint between the handle and stabilizing device.

2. Background Art

Atherosclerosis or coronary artery disease is among the most common and serious health problems confronting the medical profession. In the past, many different approaches at therapy have been utilized. Surgical correction of occluded or stenosed coronary arteries via bypass grafting through conventional approaches, such as the sternotomy, are probably still the most common procedure performed today, especially where multiple bypass grafts are needed.

However, interventional techniques, such as percutaneous transluminal angioplasty (PTCA), have gained popularity as the method of choice for therapy of atherosclerotic occlusions for several reasons. The transluminal approach is a minimally invasive technique which subjects the patient to less trauma and less recovery time, especially when compared to bypass grafts which utilize homologous tissue, such as saphenous vein grafts. Often the patient suffers complications at the graft donor site which are worse than the sternotomy and anastomosis.

Although PTCA procedures are often successful, complications such as restenosis or thrombosis and embolism can occur. Intravascular stents are sometimes deployed at the PTCA site to lessen the occurrence of restenosis. However, restenosed vessels often require surgical intervention for correction.

Surgical correction of restenosis, as well as conventional bypass graft surgery, require that the heart be stopped and the patient placed on a heart/lung bypass machine during the procedure. This occurs at considerable expense and risk to the patient. In an effort to reduce the expense, risk and trauma to the patient, physicians have recently turned to minimally invasive surgical approaches to the heart, such as intercostal and endoscopic access to the surgical site. In addition, utilization of alternative graft vessels, such as the internal mammary artery (IMA), have also greatly reduced the trauma to the patient and increased the efficacy of surgical therapy.

Prior to the present invention, however, attempts at performing minimally invasive bypass grafting on a beating heart were thought to be too tedious, dangerous and difficult because of the delicate nature of the surgical procedure, the lack of adequate access through a reduced surgical field, and the lack of a way to adequately stabilize and reduce movement at the graft site. Such a minimally invasive bypass grafting performed on the beating heart eliminates the expense and risk of stopping the heart and the necessity of the heart lung bypass machine and decreases patient recovery time. For single or double bypass procedures, especially where the IMA is utilized, patient trauma and recovery time is even further decreased.

SUMMARY OF THE INVENTION

The above problems of the prior art are overcome by the present invention which provides an apparatus for stabilizing a predetermined area on a heart or other organ of a patient to enable a surgical procedure to be performed. The apparatus of the present invention comprises a bifurcated member having two prongs, an elongated handle segment, and a means for pivotally connecting the handle segment to the bifurcated member. Each prong of the bifurcated member has a first section and a second section. The first section is adjacent the handle segment and terminates in the second section. The second section engages the heart or other organ on which the surgical procedure occurs.

The present invention also encompasses a means for movably mounting the handle segment to a rib retractor or other surgical device. The mounting means, which is preferably a swivel head, holds the bifurcated member at the predetermined site, thus alleviating the requirement that a person hold the handle segment.

Since the second section engages the heart, it is desired that the second section further comprises a means for stabilizing it from sliding on the heart. Stabilizing the apparatus on the heart is an important consideration during the surgical procedure. The present invention can encompass many different stabilizing means, including, for example, a DeBakey serrated pattern, a textured portion on at least a portion of one second section, an insert disposed on the second section having a plurality of teeth, an insert having a plurality of flexible hooks, an insert having a plurality of bristles, or even a flexible covering disposed over at least a portion of the second section. The flexible covering can be a cloth, such as cotton, or a tubular member formed from a material such as silicon.

As will be appreciated, the apparatus of the present invention can be used in surgical procedures other than heart surgery, including, for example, soft tissue procedures such as vascular thrombosis repair, intestinal resection and anastomosis and other intra-abdominal procedures, and the like.

Thus, it is an object of the invention to provide an apparatus for stabilizing a predetermined area of the heart or other organ of a patient to enable a surgeon to perform a surgical procedure at the predetermined site.

Another object of the invention is to provide an apparatus for stabilization of an area of the beating heart adjacent to a coronary artery for performing coronary artery bypass grafting.

A further object of the invention is to provide an apparatus as above that is adapted for pivotal attachment to a device that provides access to the surgical site, such as a rib spreader or other retractor.

The above recited objects of the invention are not intended to so limit the used of the invention. These and other objects of the invention will be apparent to the skilled artisan based upon the following disclosure.

BRIEF DESCRIPTION OF THE FIGURES OF THE DRAWINGS

FIG. 3 is a side view of the stabilizer shown in FIG. 1.

FIG. 4 is a bottom plan view of FIG. 3.

FIG. 5A is a perspective view of an alternate embodiment of the stabilizer of the present invention having a ball and socket pivotal connecting means.

FIG. 6 is a bottom perspective view of a portion of the bifurcated member of the present invention showing the textured surface on the second section of the prongs.

DETAILED DESCRIPTION OF THE INVENTION

The present invention is more particularly described in the following examples that are intended as illustrative only since numerous modifications and variations therein will be apparent to those skilled in the art. As used in the specification and in the claims, "a" can mean one or more, depending upon the context in which it is used.

The present invention, as shown in FIGS. 1-6, encompasses an apparatus 10 for stabilizing a predetermined area on a heart of a patient to enable a surgical procedure to be performed. The apparatus 10, or stabilizer, comprises a bifurcated member 30 that is pivotally connected to an elongated handle segment 50. The handle segment 50 is preferably movably mounted to a rib spreader 20 or other similar equipment that remains stationarily positioned on or adjacent to the patient during a surgical procedure.

Figure 1:
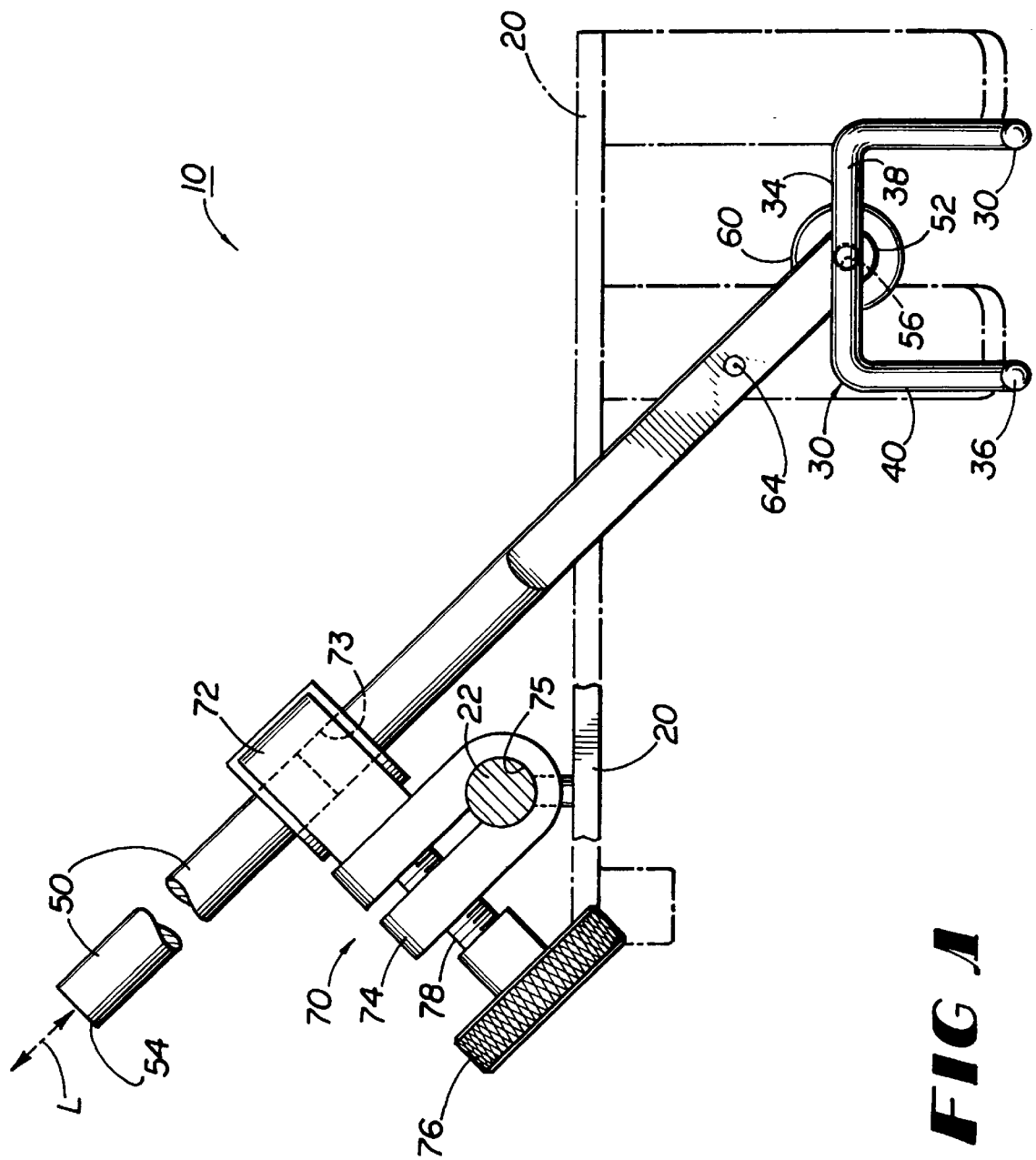
FIG. 1 is a side view of one embodiment of the present invention showing the stabilizer mounted to a rib retractor.
Figure 2:
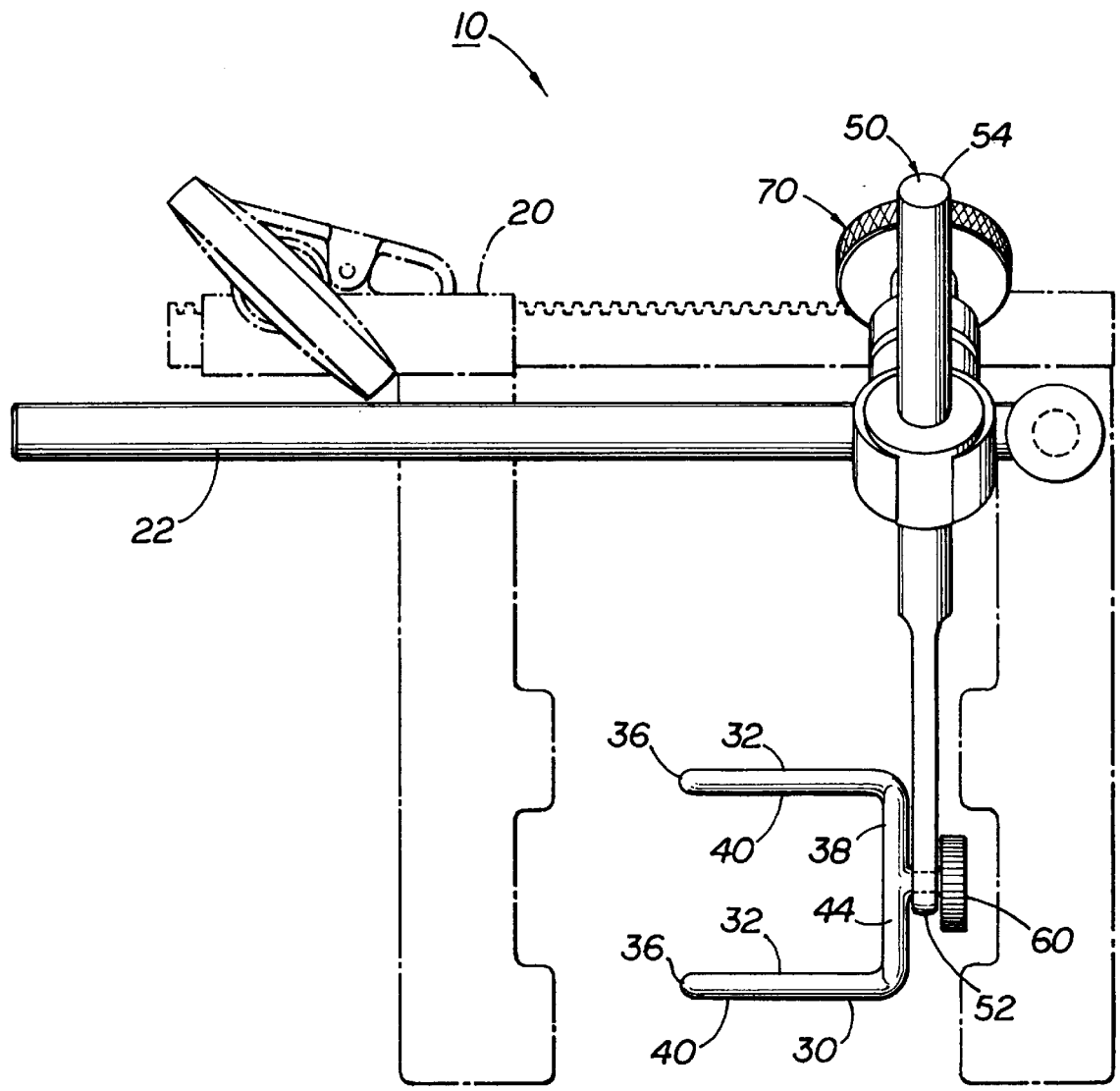
FIG. 2 is a top plan view of FIG. 1.

The present invention is ideal for use in heart surgery, in either conventional open heart surgery or by minimally invasive surgery, e.g., minimally invasive coronary artery bypass grafting. For minimally invasive surgery, access to the heart may be achieved through the ribs of the patient using a rib spreader 20, as shown in FIGS. 1 and 2. In the typical procedure, the surgeons will access the heart via the fourth intercostal space located between the third and fourth ribs, but this may be changed based on the individual patient's anatomy. Since, for the above reasons, this procedure is sometimes performed on a beating heart, it is advantageous to stabilize the heart in the area that the surgical procedure will occur.

When the present invention engages the surface of the heart, the surgeon applies a slight compressive force on the heart with the apparatus 10 in the area that the surgical procedure will occur so that the heart's movement at that specific area is diminished and stabilized. Stabilizing the heart is particularly useful for a heart suturing technique in the area of the coronary arteries such as the anastomosis of a bypass graft. In particular, it is advantageous to place a traction suture around an artery using a needle and suture thread while the present invention is stabilizing the surface of the heart adjacent to the artery. One skilled in the art will appreciate that the present invention, although ideal for heart surgery, can be used at any location on or within the body where tissue stabilization or isolation of a predetermined area is desired, including but not limited to the liver, kidneys, bladder, stomach, intestines, and vascular and other soft tissue surgery.

The bifurcated member 30 of the present invention has two elongated prongs 32 in which each prong 32 has a proximal end 34 and an opposite distal end 36 and each prong 32 forms a first section 38 and a second section 40. The prongs 32 are attached to each other adjacent their proximal ends 34. The first section 38 of each prong 32 is adjacent the proximal end 34 and terminates in the second section 40, and the second section 40 is adjacent the distal end 36. The second section 40 is adapted to engage a predetermined area on the heart or other organ of the patient.

A third section 42, shown in FIG. 6, can be added to at least one of the prongs 32 at the end of the second section 40 that is opposite the first section 38. The third section 42 can be used as a tissue retractor or a retractor to pull a selected item, such as surgical thread, away from the area that the surgical procedure is being performed. In addition, the third section 42 can be advantageously positioned to secure surgical thread to a cleat (not shown) disposed on the handle segment 50.

As best shown in FIG. 3, a connecting member 44 is disposed intermediate the proximal end 34 of each prong 32, instead of directly connecting the prongs 32 to each other. The connecting member 44 has opposed ends in which each end is attached to the proximal end 34 of a respective prong 32. As one skilled in the art will appreciate, the length of the first section 38 can be very short so that the connecting member 44 would be either attached directly to or slightly separated from the second section 40. However, this alternate embodiment is not desirable because a separation height of at least a quarter (¼) of an inch is desired between the surface of the heart and the connecting member 44, to which the attached handle segment 50 is attached.

The handle segment 50 is used to extend the bifurcated member 30 into the chest of the patient to reach the surface of the heart. The handle segment 50 has a first end 52 and an opposite second end 54. The handle segment 50 also has a longitudinal axis L and defines a bore 56 therethrough. The bore 56 is disposed adjacent the first end 52 of the handle segment 50 and extends substantially perpendicular to its longitudinal axis L.

The stabilizer 10 of the present invention also comprises a means for pivotably connecting the first end 52 of the handle segment 50 to the two prongs 32 of the bifurcated member 30 adjacent their proximal ends 34. In the preferred embodiment shown in FIGS. 1–4, the pivotal connecting means comprises a positioning member 60 and a rod 62 rotatably disposed through the bore 56 in the handle segment 50. The rod 62 has opposed ends and a length extending therebetween. One end of the rod 62 is fixedly attached to the positioning member 60 and the opposed end of the rod 62 is fixedly attached to the connecting member 44 so that the bifurcated member 30 is at least partially rotatable about an axis of rotation R, which is parallel to and disposed through the bore 56 of the handle segment 50. Preferably, the length of the rod 62 is of a size to allow rotation of the bifurcated member 30 but to prevent transverse, or lateral, movement of the bifurcated member 30 relative to the longitudinal axis L of the handle segment 50. That is, the bifurcated member 30 is rotatable but does not have undesirable lateral play.

As shown in FIG. 1, the stabilizer 10 can use a pin 64 fixedly attached to a portion of the handle segment 50 intermediate its first and the second ends 52, 54. The pin 64 is disposed to block complete rotation of the bifurcated member 30 so that bifurcated member 30 is rotatable less than 360° about the bore 56 of the handle segment 50. This prevents the bifurcated member 30 flipping to an inverted position when the surgeon is placing the second section 40 of the prongs 32 on the heart of the patient.

The advantage of the pivotal connecting means— compared to another joining means in which the handle section is not movable relative to the bifurcated member 30—is that the second sections 40 can be disposed at the predetermined location and the handle segment 50 oriented to a position that does not interfere with the surgeon performing the surgical procedure. That is, once the bifurcated member 30 is properly positioned, then the handle segment 50 is moveable to a position and, optionally, locked at that position by a mechanical device so that the handle segment 50 does not interfere with the surgery by one mechanical device, such as a swivel head.

Referring now to FIG. 5A, an alternative embodiment of the pivotal connecting means comprises a socket 68 disposed on the first end 52 of the handle segment 50 and a ball 66 joined to the proximal ends 34 of the two prongs 32 of the bifurcated member 30. The ball 66 is sized to be complementarily received within the socket 68. Preferably, the pivotal connecting means further comprises a means for locking the ball 66 in a selective position within the socket 68 so that the handle segment 50 is disposed at a desired orientation relative to the second sections 40. An example is a tightener 69 that constricts the size of the socket 68 to lock the ball 66 in the desired position.

Figure 5B:
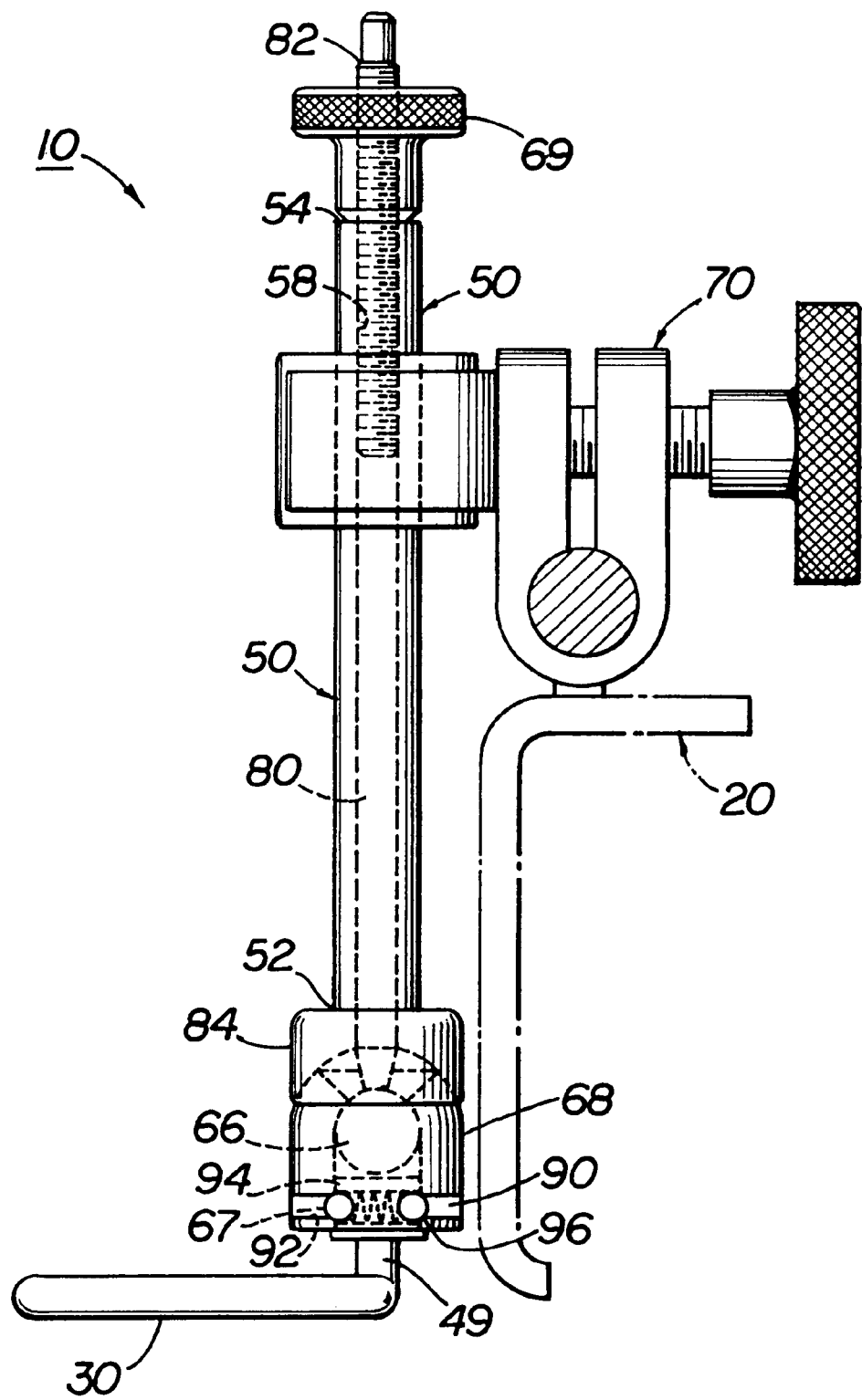
FIG. 5B is a side cross-sectional view of an alternate embodiment of the stabilizer having a ball and socket pivotal connecting means in which the bifurcated member is interchangeable.

Referring now to FIG. 5B, an alternate embodiment of the ball and socket pivotal connecting means of FIG. 5A is shown. A longitudinally-extending shaft 80, which is disposed through a longitudinal bore 58 in the handle segment 50, is fixedly attached to the ball 66. The upper end 82 of the shaft 80 is threaded so that the complementarily-threaded tightener 69 controls longitudinal movement of the shaft 80 and the attached ball 66 relative to the handle segment 50. The bifurcated member 30 is attached to the socket 68 adjacent its bottom end 67. When the surgeon tightens the tightener 69, the ball 66 is moved toward the handle segment 50, which has a bowlshaped member 84 attached adjacent its first end 52. The bowl-shaped member 84 is of a size to received a portion of the socket 68 therein. Thus, turning the tightener 69 moves the ball 66 toward the first end 52 of the handle segment 50, which correspondingly moves the socket 68 into the bowl-shaped member 84. The surgeon continues to turn the tightener 69 until the socket 68 is securably seated in the bowl-shaped member 84 with the bifurcated member 30 at a desired orientation. As shown in FIG. 5B, the socket 68 allows the shaft 80 to be rotated thirty degrees (30°) in all directions relative to its centerline, but can be designed to allow rotation up to ninety degrees (90°).

Other pivotal connecting means are contemplated including, for example, a hinged connection (not shown) in which the handle segment 50 only pivots in a plane that is perpendicular to the plane formed by the second sections 40.

The present invention can further comprise a means for interchangeably mounting the pivotal attached bifurcated member 30. Still referring to FIG. 5B, the bifurcated member 30 is detachably secured to the socket 68 and is interchangeable with another bifurcated member 30 in which the prongs 32 have a different dimension or separation distance. The socket 68 has a detent 90 in its interior side adjacent its bottom end 67. The connecting member 49 is attached to a plunger device 92 that has a shell 94 containing at least one circular member 96 and a means for biasing the circular members 96 away from the center of the shell 94. An example of the biasing means is a spring (not shown).

The shell 94 is of a size to be complementarily received in the interior of the socket 68 adjacent its bottom end 67 when no portion of the circular member 96 extends outwardly from the shell 94. As one skilled in the art will appreciate, when the shell 94 is pushed into the socket 68, the normally outwardly-projecting circular member 96 is forced toward the center of the shell 94 against the opposing force of the biasing means. Once the shell 94 is pushed far enough into the socket 68 for the circular member 96 to align with the detent 90, the biasing means will force the circular member 96 away from the center of the shell 94 and into the detent 90. The shell 94 will remain detachably secured in this position until a force is applied to the shell 94, such as downwardly pulling on the bifurcated member 30, to overcome the force of the biasing means. Thus, the bifurcated members 30 are interchangeable in the present invention, which is advantageous for different patients or changes in circumstances that arise during the surgical procedure.

In an alternate embodiment, the interchangeably mounting means comprises the interior surface of the socket 68 having a threaded surface (not shown) and a portion of the shell 94 having a complementarily threaded surface (not shown) that detachably connects to the socket 68. However, this alternate embodiment is less desirable because it could allow rotation of the bifurcated member 30 to occur.

In the preferred embodiment, the present invention further comprises a means for movably mounting the handle segment 50 to a rib retractor 20. Referring to FIGS. 1 and 2, it is preferred that the mounting means comprises a swivel head 70 having a first portion 72, a second portion 74, and a tightening portion 76. The first portion 72 defines a slot 73 therethrough which is of a size to slidably and adjustably receive a portion of the handle segment 50 therein. The handle segment 50, accordingly, is movable in the slot 73 longitudinally and rotationally relative to the first portion 72 of the swivel head 70.

The second portion 74 defines an opening 75 therethrough which is adapted to detachably and slidably engage a portion of the rib retractor 20, preferably, an elongated slide segment 22. That is, the second section 40 allows movement of the handle segment 50 and attached bifurcated member 30 in all directions relative to the slide segment 22. The second section 40 is slidable along the slide segment 22 and is pivotal transversely relative to the slide segment 22. Furthermore, the handle segment 50 is rotatable so that its longitudinal axis L can form different angles relative to the length, or longitudinal axis, of the slide segment 22. The handle segment 50 thus is movable to any position except where the swivel head 70, handle segment 50, or bifurcated member 30 are blocked by an obstruction, such as a portion of the rib retractor 20. This freedom of movement, coupled with the movement that the pivotal connecting means and first portion 72 provides, allow the surgeon the greatest flexibility to dispose the second section 40 of each prong 32 on the heart while the handle segment 50 is movably connected to the rib retractor 20.

An advantage of the present invention is that the handle segment 50 and bifurcated member 30 can be pre-aligned so that the bifurcated member 30 is self-positioning on the patient's heart by lowering the handle segment 50. Once the surgeon lowers the bifurcated member 30 to the desired position, the surgeon can then maintain the second sections 40 engaging the heart while re-orienting the handle segment 50, if required, to a position that allows the greatest access to the surgery site. When the handle segment 50 is at the desired orientation, the tightening portion 76 of the swivel head 70 is tightened, preferably by a single turn of the tightening portion 76, to secure the handle segment 50 at a desired position.

The tightening portion 76 operates by a screw member 78 disposed through a section of the swivel head 70 tightening the first and second portions 72, 74 in place. Thus, the tightening portion 76 detachably secures the handle segment 50 at a desired orientation in the slot 73 of the first portion 72 and the swivel head 70 at a desired position on the rib retractor 20 so that the surgeon is free to perform the surgical procedure. The tightened portion can be easily loosened, when desired, to allow the handle segment 50 and the bifurcated member 30 to be moved.

The handle segment 50 thus is held in the desired position by a connection with the rib retractor 20 that is necessary to preform the surgical procedure. As shown best in FIG. 2, the stabilizer 10 can be disposed to the side of the rib retractor 20 so that it allows a wide angle of access to the surgical site. An undesirable alternative is to have another surgeon or nurse hold the handle segment 50 during the surgical procedure, which creates problems with space constraints, fluctuations in the pressure of the second sections 40 on the heart, and increased costs for the extra person to hold the handle segment 50.

As one skilled in the art will appreciate, there are numerous other options available to mount the handle segment 50 to the rib retractor 20 or other surgical equipment so that the second section 40 is maintained at a desired position without a person physically holding the apparatus 10. One example of such a mounting means is a ball and socket connection (not shown). However, it has been found that the swivel head is a more desirable mounting means because of the control and ease of locking the bifurcated member 30 and handle segment 50 at the desired position.

Referring back to FIGS. 3 and 4, the second section 40 each of the two prongs 32 is preferably disposed substantially perpendicular to the longitudinal axis L of the handle segment 50, regardless of the direction that the bifurcated member 30 pivots. It is also preferred that the second sections 40 of each of the two prongs 32 are co-planar and that the juncture between the first section 38 and the second section 40 of the prongs 32 of the bifurcated member 30 form an approximately 90°, or right, angle φ therebetween, as shown in FIG. 6. A right, or even obtuse, angle φ is preferred so that the surgeon has better access to the area that the surgical procedure is performed. An acute angle could be used, but it is less desirable because it would likely interfere with the surgical procedure.

For use in heart surgery, the apparatus 10 has certain size limitations. For example, the available area to a surgeon to perform a minimally invasive surgical procedure on the heart via an intercostal approach is approximately three (3) inches by one and a half (1½) inches, which, of course, may vary between patients. Accordingly, it is desired that the width between the second sections 40 be in the range of one half (½) to one and a quarter (1¼) inches, more preferably in the range of three quarters (¾) of an inch to one (1) inch. These widths are narrow enough to fit into the confined space, yet wide enough to bridge the area of interest, e.g., bridge an artery that is to be bypassed.

In a preferred embodiment, the length of the second section 40 is in the range of one half (½) inch to one and a half (½) inches, more preferably in the range of two-thirds (⅔) of an inch to three quarters (¾) of an inch. In the preferred embodiment, each second section 40 is one (1) inch long and separated by three quarters (¾) of an inch to one (1) inch from the other second section 40.

Since the second section 40 engages the heart, it is preferable that this section further comprise a means for stabilizing the second section 40 from sliding on the heart when in contact therewith. That is, the stabilizing means resists sliding or slipping motion between the surface of the heart and the second section 40. The stabilizing means increases the coefficient of friction but should not have a texture that may potentially damage tissue of the heart or other vital organs.

In one embodiment shown in FIG. 6, the stabilizing means comprises a textured surface 46 which is a knurled texture. Other embodiments are contemplated, such as a DeBakey serrated pattern (not shown) or a plurality of intersecting slits (not shown) that prevent the second section 40 from sliding when it engages the heart. As one skilled in the art will appreciate, other stabilizing means can be used so long as the stabilizing means atraumatically grips the tissue.

Another contemplated embodiment of the stabilizing means includes a removable insert (not shown) having an attaching surface secured to the second section 40 of each prong 32 and an opposite stabilizing surface (not shown) which carries the stabilizing means. The stabilizing surface of the insert can comprise a plurality of tungsten carbide or stainless steel teeth forming the DeBakey or other pattern. Another embodiment is that the stabilizing surface comprises a plurality of flexible hooks (not shown). The preferred hooks are those of a hook and loop fastener, commonly referred to as VELCRO® fasteners. Still another embodiment comprises a plurality of bristles (not shown) in which the bristles are disposed at a plurality of different orientations, similar to that of a tube or glass cleaner. Because of the multiple orientations of the bristles, any direction that the second section 40 tends to slide is resisted by bristles oriented that direction that contact the surface of the heart to resist the motion.

Yet another embodiment of the stabilizing means comprises a flexible covering disposed over at least a portion of the second section 40. The covering can be a cloth, such as cotton, braided cotton, linen or other coverings that resist motion when disposed on the surface of a heart. Similarly, the covering can be a tubular member selected from the group of silicon, rubber, or plastic as well as other materials that resist motion when disposed on the surface of a heart.

Although the present invention has been described with reference to specific details of certain embodiments thereof, it is not intended that such details should be regarded as limitations upon the scope of the invention except as and to the extent that they are included in the accompanying claims.

What is claimed is:

1. An apparatus for stabilizing a predetermined area of a heart, the apparatus comprising:

a. a bifurcated member having two elongated prongs, each prong having a proximal end and an opposite distal end and having a second section, the prongs being attached to each other adjacent the proximal ends thereof, the second section of each prong being adapted to engage a heart of a patient;

b. an elongated handle segment having a first end portion, an opposite end portion, a longitudinal axis and defining a bore therethrough, the bore being disposed adjacent the first end portion thereof and extends transversely relative to the longitudinal axis of the handle segment and the opposite second end portion of the handle segment is operatively connected to a rib retractor; and c. a connecting member for pivotally connecting the first end portion of the handle segment to the bifurcated member, wherein the connecting member comprises:

i. a positioning member; and ii. a rod having opposed end portions and a length extending therebetween, the rod being rotatably disposed through the transversely extending bore in the handle segment, one end portion of the rod being attached to the positioning member and the opposed end portion of the rod being attached to the bifurcated member so that the bifurcated member is at least partially rotatable about the bore of the handle segment.

2. The apparatus of claim 1, wherein the second section of at least one prong further comprises means for stabilizing the second section from sliding on the heart when in contact therewith.

3. The apparatus of claim 1, wherein the second section of each of the two prongs are in the same plane.

4. A stabilizer comprising:
   a. a bifurcated member having two elongated prongs, each prong having a proximal end and an opposite distal end and having a second section, the prongs being attached to each other adjacent the proximal ends thereof, the second section of each prone being adapted to engage a heart of a patient;
   b. an elongated handle segment having a first end, an opposite second end, a longitudinal axis and defining a bore therethrough, the bore being disposed adjacent the first end thereof and extending transversely relative to the longitudinal axis;
   c. means for pivotally connecting the first end of the handle segment to the two prongs of the bifurcated member adjacent the proximal ends thereof, wherein the pivotal connecting means comprises:
      i. a positioning member; and
      ii. a rod having opposed ends and a length extending therebetween, the rod being rotatably disposed through the bore in the handle segment, one end of the rod being fixedly attached to the positioning member and the opposed end of the rod being fixedly attached to a portion of the bifurcated member so that the bifurcated member is at least partially rotatable about the bore of the handle segment; and
   d. a swivel head having a first portion, a second portion, and a tightening portion, the first portion defining a slot therethrough which is of a size to slidably and adjustably receive a portion of the handle segment therein, the second section defining an opening therethrough which is adapted to detachably and slidably engage a portion of a rib retractor, and the tightening portion being adapted to secure the handle segment at a desired position in the slot of the first portion and to secure the swivel head at a desired position on the rib retractor.

5. A stabilizer, comprising:
   a. a bifurcated member having two elongated prongs, each prong having a proximal end and an opposite distal end and having a second section, the prongs being attached to each other adjacent the proximal ends thereof, the second section of each prong being adapted to engage a heart of a patient;
   b. an elongated handle segment having a first end, an opposite second end. a longitudinal axis and defining a bore therethrough, the bore being disposed adjacent the first end thereof and extending transversely relative to the longitudinal axis;
   c. means for pivotally connecting the first end of the handle segment to the two prongs of the bifurcated member adjacent the proximal ends thereof, wherein the pivotal connecting means comprises:
      i. a positioning member; and
      ii. a rod having opposed ends and a length extending therebetween, the rod being rotatably disposed through the bore in the handle segment, one end of the rod being fixedly attached to the positioning member and the opposed end of the rod being fixedly attached to a portion of the bifurcated member so that the bifurcated member is at least partially rotatable about the bore of the handle segment; and
   d. means for mounting the handle segment to a rib retractor.

6. The stabilizer of claim 5, wherein the mounting means comprises a swivel head having a first portion, a second portion, and a tightening portion, the first portion defining a slot therethrough which is of a size to slidably and adjustably receive a portion of the handle segment therein, the second section defining an opening therethrough which is adapted to detachably and slidably engage a portion of the rib retractor, and the tightening portion being adapted to secure the handle segment at a desired position in the slot of the first portion and to secure the swivel head at a desired position on the rib retractor.

7. An apparatus, comprising:
   a. a bifurcated member having two elongated prongs, each prong having a proximal end and an opposite distal end and having a first section and a second section, the prongs being attached to each other adjacent the proximal ends thereof, the first section of each prong being adjacent the proximal end of the prong, the second section of each prong being adjacent the distal end of the prong and being adapted to engage a heart of a patient;
   b. an elongated handle segment having a first end and an opposite second end;
   c. means for pivotally connecting the first end of the handle segment to the two prongs of the bifurcated member adjacent the proximal ends thereof; and
   d. means for mounting the handle segment to a rib retractor,
   wherein the bifurcated member further comprises a connecting member disposed intermediate the proximal end of each prong, the connecting member having opposed ends in which each end is attached to the proximal end of a respective prong,
   wherein the handle segment has a longitudinal axis and defines a bore therethrough, the bore being disposed adjacent the first end thereof and extending transversely relative to the longitudinal axis thereof, and
   wherein the pivotal connecting means comprises:
      i. a positioning member; and
      ii. a rod having opposed ends and a length extending therebetween, the rod being rotatably disposed through the bore in the handle segment, one end of the rod being fixedly attached to the positioning member and the opposed end of the rod being fixedly attached to the connecting member so that the bifurcated member is at least partially rotatable about the bore of the handle segment.

8. The apparatus of claim 7, wherein the mounting means comprises a swivel head having a first portion, a second portion, and a tightening portion, the first portion defining a slot therethrough which is of a size to slidably and adjustably receive a portion of the handle segment therein, the second section defining an opening therethrough which is adapted to detachably and slidably engage a slide segment of the rib retractor, and the tightening portion being adapted to secure the handle segment at a desired position in the slot of the first portion and to secure the swivel head at a desired position on the rib retractor.

9. The apparatus of claim 7, wherein the second section each of the two prongs of the bifurcated member is disposed substantially perpendicular to the longitudinal axis of the handle segment.

10. The apparatus of claim 7, wherein the second section of at least one prong further comprises means for stabilizing the second section from sliding on the heart when in contact therewith.

11. The apparatus of claim 10, wherein the stabilizing means comprises a textured surface on the second section of one prong, the textured surface being a DeBakey serrated pattern.

12. The apparatus of claim 7, further comprising means for interchangeably mounting the bifurcated member to the pivotal connecting means.

13. An apparatus for stabilizing a predetermined area of a heart, the apparatus comprising:
  a. a stabilizing device having a first surface sized to contact the predetermined area of the heart of a patient and a second surface thereon;
  b. an elongated handle member having a first end, an opposite second end, a longitudinal axis and defining a bore therethrough, the bore being disposed adjacent the first end of the handle member and extending transversely relative to the longitudinal axis thereof;
  c. a connecting member for pivotally connecting the second surface of the stabilizing device to the first end of the handle member, wherein said connecting member includes a positioning member and a rod having opposed ends and a length extending therebetween, the rod being rotatably disposed through the bore in the handle segment, one end of the rod being fixedly attached to the positioning member and the opposed end of the rod being fixedly attached to a portion of the stabilizing device so that the stabilizing device is at least partially rotatable about the bore of the handle segment; and
  d. a swivel head having a first portion, a second portion, and a tightening portion, the first portion defining a slot therethrough which is of a size to slidably and adjustably receive a portion of the handle segment therein, the second section defining an opening therethrough which is adapted to detachably and slidably engage a portion of a rib retractor, and the tightening portion being adapted to secure the handle segment at a desired position in the slot of the first portion and to secure the swivel head at a desired position on the rib retractor.

14. An apparatus for stabilizing a predetermined area of a heart, the apparatus comprising:
  a. a stabilizing device having a first surface sized to contact the predetermined area of the heart of a patient and a second surface thereon;
  b. an elongated handle member having a first end portion, an opposite second end portion, a longitudinal axis and defining a bore therethrough, the bore being disposed adjacent the first end portion of the handle member and extending transversely relative to the longitudinal axis thereof;
  c. a connecting member for pivotally connecting the second surface of the stabilizing device to the first end portion of the handle member wherein said connecting member includes a positioning member and a rod having opposed end portions and a length extending therebetween, the rod being rotatably disposed through the transversely extending bore in the handle segment, one end portion of the rod being attached to the positioning member and the opposed end portion of the rod being attached to the stabilizing device so that the stabilizing device is at least partially rotatable about the bore of the handle segment; and
  d. a mounting member operatively connected to the second end portion of the handle segment for mounting the handle segment to a rib retractor.

* * * * *

UNITED STATES PATENT AND TRADEMARK OFFICE
CERTIFICATE OF CORRECTION

PATENT NO.  : 6,132,370
DATED       : October 17, 2000
INVENTOR(S) : Gregory R. Furnish and Christopher S. Looney It is certified that error appears in the above-identified patent and that said Letters Patent is hereby corrected as shown below:

Title page,
Columns 1-2, under "References Cited", add the following:

References Cited
U.S. PATENT DOCUMENTS

| | | |
|---|---|---|
| 5,449,374 | 9/95  | Dunn et al. |
| 5,518,503 | 5/96  | Rooney et al. |
| 5,222,976 | 6/93  | Yoon |
| 5,201,325 | 4/93  | McEwen et al. |
| 3,943,592 | 3/76  | Bhaskar et al. |
| 4,616,634 | 10/86 | Vargas Garcia |
| 5,429,118 | 7/95  | Cole et al. |
| 3,882,855 | 5/75  | Schulte et al. |
| 5,558,621 | 9/96  | Heil |
| 3,409,013 | 11/68 | Berry |
| 4,457,300 | 7/84  | Budde |
| 5,337,736 | 8/94  | Reddy |
| 5,509,890 | 4/96  | Kazama |

FOREIGN PATENT DOCUMENTS

| | | |
|---|---|---|
| 970751 | 8/21/97 | Norway |
| 970752 | 8/21/97 | Norway |
| 970753 | 8/21/97 | Norway |
| 970754 | 8/21/97 | Norway |

Signed and Sealed this

Eleventh Day of December, 2001

*Attest:*

NICHOLAS P. GODICI
*Attesting Officer          Acting Director of the United States Patent and Trademark Office*